(12) United States Patent
Gelbien

(10) Patent No.: US 12,097,057 B1
(45) Date of Patent: Sep. 24, 2024

(54) PATIENT POSITIONING SYSTEM FOR USE IN AN MRI SCANNER

(71) Applicant: Fonar Corporation, Melville, NY (US)

(72) Inventor: Mark Gelbien, Plainview, NY (US)

(73) Assignee: Fonar Corporation, Melville, NY (US)

( * ) Notice: Subject to any disclaimer, the term of this patent is extended or adjusted under 35 U.S.C. 154(b) by 732 days.

(21) Appl. No.: 16/667,062

(22) Filed: Oct. 29, 2019

Related U.S. Application Data

(60) Provisional application No. 62/752,531, filed on Oct. 30, 2018.

(51) Int. Cl.
*A61B 6/04* (2006.01)
*A61B 5/055* (2006.01)
(Continued)

(52) U.S. Cl.
CPC .......... *A61B 6/0487* (2020.08); *A61B 5/055* (2013.01); *A61B 6/00* (2013.01); *A61B 6/0407* (2013.01); *A61G 7/018* (2013.01); *A61G 7/1032* (2013.01); *A61G 13/02* (2013.01); *B62B 5/04* (2013.01); *B62B 5/0428* (2013.01)

(58) Field of Classification Search
CPC ....... A61B 6/0407; A61B 6/0471; A61B 6/00; A61B 6/0487; A61B 17/2255; A61B 5/055; A61G 13/06; A61G 13/08; A61G 13/04; A61G 13/02; A61G 7/002; A61G 7/005; A61G 7/012; A61G 7/015; A61G 7/018; A61G 7/1032; A61G 7/1034; A61G 1/003; B62B 2301/256; B62B 5/04; B62B 5/0428; Y10S 5/943; B65G 2812/02128; B65G 2812/02148; B65G 2812/02138
See application file for complete search history.

(56) References Cited

U.S. PATENT DOCUMENTS 5,797,606 A * 8/1998 Misawa ................ A61G 5/066
280/5.22
9,956,128 B1 * 5/2018 Phillips .................... A61G 7/16
(Continued)

OTHER PUBLICATIONS https://www.merriam-webster.com/dictionary/horizontal (Year: 2016).*
(Continued)

*Primary Examiner* — David R Hare
*Assistant Examiner* — Deborah Talitha Gedeon
(74) *Attorney, Agent, or Firm* — Lerner David LLP

(57) ABSTRACT

A patient positioning system includes a vertical link member and a carriage sub-system pivotably mounted thereto. The carriage sub-system includes a carriage having a first end and a second end, a first guide movably coupled to the carriage and having a first end and a second end, a first connecting shaft pivotably coupled to the first ends of the first guide and the second guide, and a second connecting shaft pivotably coupled to the second ends of the first guide and the second guide. The system further includes a patient bed mounted to the carriage sub-system and a motor drive system including a motor drive, a belt configured to be driven by the motor drive, a rotation brake system configured to selectively engage with or disengage from the carriage, and a slab brake system configured to selectively engage with or disengage from the first and second connecting shafts.

15 Claims, 9 Drawing Sheets

(51) Int. Cl.
  *A61B 6/00*     (2024.01)
  *A61G 7/018*    (2006.01)
  *A61G 7/10*     (2006.01)
  *A61G 13/02*    (2006.01)
  *B62B 5/04*     (2006.01)

(56) References Cited

U.S. PATENT DOCUMENTS

| | | | | |
|---|---|---|---|---|
| 2005/0285595 | A1* | 12/2005 | Green | A61B 5/055 |
| | | | | 324/307 |
| 2006/0037789 | A1* | 2/2006 | Kritman | A61G 5/066 |
| | | | | 280/5.22 |
| 2008/0086816 | A1* | 4/2008 | Farooqui | F16M 11/42 |
| | | | | 5/601 |
| 2009/0289633 | A1* | 11/2009 | Dutto | G01R 33/307 |
| | | | | 324/318 |
| 2013/0312191 | A1* | 11/2013 | Szeinberg | A61G 7/0573 |
| | | | | 5/632 |

OTHER PUBLICATIONS

"Associated." Merriam-Webster Dictionary, Feb. 4, 2024, www.merriam-webster.com/dictionary/associated. (Year: 2024).*

* cited by examiner

PATIENT POSITIONING SYSTEM FOR USE IN AN MRI SCANNER

CROSS-REFERENCE TO RELATED APPLICATION

The present application claims the benefit of the filing date of U.S. Provisional Patent Application No. 62/752,531 filed Oct. 30, 2018, the disclosure of which is hereby incorporated herein by reference.

FIELD OF THE INVENTION

The invention generally relates to the field of MRI systems, and more particularly to a patient positioning system for use in an MRI scanner.

BACKGROUND OF THE INVENTION

Patients undergoing various medical procedures or treatments often need to be positioned correctly to properly receive a diagnosis or treatment. For instance, magnetic resonance imaging (MRI) systems require that the portion of the anatomy to be scanned be positioned within a relatively small imaging volume. One problem with some present patient positioning systems is that it is difficult to consistently and accurately locate the patient within the imaging volume to obtain a high quality image.

Moreover, MRI scanners generally require the patient to be oriented with the long axis of the body in a horizontal position. However, other positions of the body, such as vertical, horizontal, in-between angles, the Trendelenburg or reverse Trendelenburg positions, or sitting are also desirable.

Another problem is that present systems are limited in the number of positions a patient can be located in and there is no simple method of changing positions quickly for a variety of patients.

BRIEF SUMMARY OF THE INVENTION

Patient positioning systems for MRI scanners have certain unique requirements to avoid distorting an MRI image. For instance, the positioning systems preferably include non-metallic and non-conductive materials. Still further, such positioning systems need to work in a limited space within a strong magnetic field and be configured to position a patient precisely within the scanner. MRI systems produce strong Radio Frequency magnetic and electric fields. As such, if patient positioning systems are improperly or inadequately designed, a patient may be harmed, for example, by RF burns. Aspects of the present invention may address one or more of these requirements.

According to an embodiment of the disclosed technology, a positioning system comprises at least one vertical link member, a carriage sub-system mounted to the at least one vertical link member and comprising a carriage, a patient sub-system mounted to the carriage, and a drive system. The drive system comprises an actuator configured to drive the carriage, a drive configured to drive the actuator, and a slab brake system configured to selectively constrain a motion of the actuator.

According to an embodiment of the disclosed technology, a positioning system comprises at least one vertical link member and a carriage sub-system pivotably mounted to the at least one vertical link member. The carriage sub-system includes a carriage having a first end and a second end, a first guide movably coupled to the carriage and having a first end and a second end, a first connecting shaft pivotably coupled to the first ends of the first guide and the second guide, and a second connecting shaft pivotably coupled to the second ends of the first guide and the second guide. The positioning system further comprises a patient bed mounted to the carriage sub-system and a motor drive system. The motor drive system comprises a motor drive, a belt configured to be driven by the motor drive, a rotation brake system configured to selectively engage or disengage from the carriage, and a slab brake system configured to selectively engage or disengage from the first and second connecting shafts. The belt is coupled at a first end to the first end of the carriage and at a second end to the second end of the carriage. The belt is in contact engagement with the first connecting shaft between the motor drive and the first end of the carriage and with the second connecting shaft between the motor drive and the second end of the carriage.

According to an embodiment of the technology, the positioning system further comprises a lift sub-system configured to adjust a height of the carriage sub-system. The lift sub-system comprises a parallelogram structure that includes the at least one vertical link member, a second vertical link member, a first horizontal link member, and a second horizontal link member. The at least one vertical link member and the second vertical link member are pivotably connected to the first and second horizontal link members.

According to another embodiment of the disclosed technology, a patient positioning system comprises a lift sub-system, a carriage sub-system mounted on the lift sub-system and comprising a carriage, and a patient bed sub-system mounted to the carriage. The lift sub-system comprises a first parallelogram comprising a first vertical link member, a second vertical link member, a first horizontal link member, and a second horizontal link member. Each of the first vertical link member and the second vertical link member is pivotably connected to the first horizontal link member and the second horizontal link member.

According to an aspect of the technology, a method of positioning a bed comprises translating a bed, rigidly coupled to a carriage, along a first translating axis by driving an actuator coupled to a first end of the carriage at a first end of the actuator and to a second end of the carriage at a second end of the actuator and causing the carriage to move along a first guide and a second guide, and/or pivoting the bed along a pivoting axis by driving the actuator and causing the carriage to pivot along the pivoting axis.

DETAILED DESCRIPTION

The following detailed description, which references and incorporates the figures, describes and illustrates one or more specific embodiments of the disclosed technology. These embodiments, offered not to limit but only to exemplify and teach the disclosed technology, are shown and described in sufficient detail to enable those skilled in the art to implement the technology and/or to practice the invention. Thus, where appropriate to avoid obscuring features of the disclosed technology, the description may omit certain information known to those of skill in the art. It will further be understood that, while various components are identified individually for the ease of understanding, one or more of these components may be part of a unitary structure or may be integrally manufactured.

Figure 1:
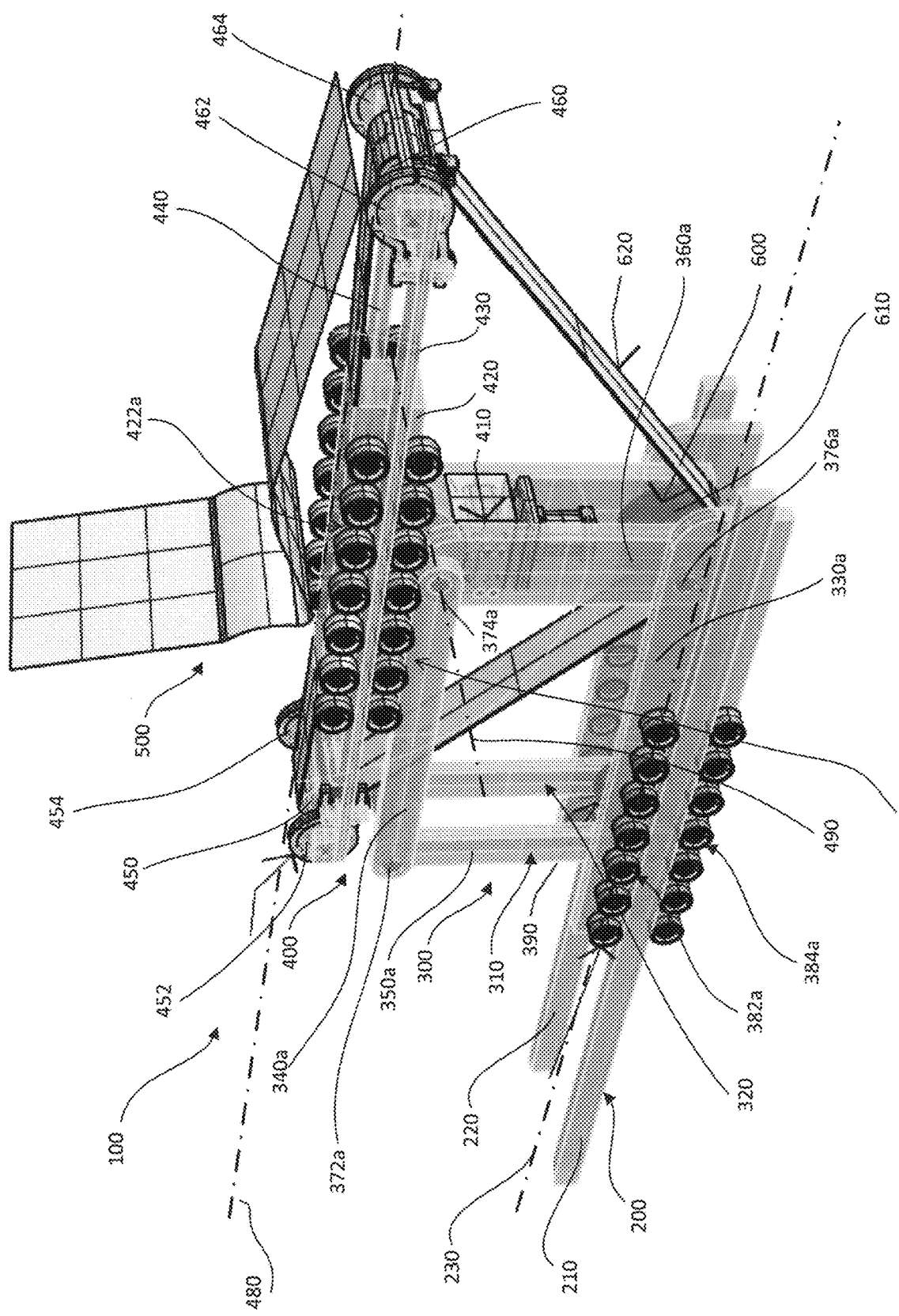
FIG. 1 shows a front isometric view of a patient positioning system according to one embodiment of the technology.

FIG. 1 shows a patient positioning system 100 according to an embodiment. The patient positioning system 100 is a multi-axis positioning system, which can be used to articulate a patient's anatomy in various orientations. In various embodiments, the present positioning system can be used for positioning humans, animals, inanimate objects and so on. Accordingly, the term patient generally includes any object being positioned by the positioning system.

The patient positioning system 100 includes a guide sub-system 200, a lift sub-system 300, a carriage sub-system 400, and a bed sub-system 500 mounted on the carriage sub-system. In an exemplary embodiment, the guide sub-system 200 includes first and second guide rails 210, 220 for guiding the bed sub-system 500 in and out of, for example, the MRI scanner. The first and second guide rails 210, 220 extend along a first longitudinal axis 230. The first and second guide rails 210, 220 are preferably made of a non-metallic, non-conductive material such as a composite material, for example, a fiberglass material such as G10 or a composite material composed of woven fiberglass cloth with an epoxy resin binder that is flame resistant, such as FR4. Any other magnetically translucent material which has sufficient mechanical strength to guide and support all the components of the patient positioning system 100 may also be used. While the illustrated embodiment includes two guide rails, it will be understood that other embodiments may have less than or more than two guide rails, without departing from the scope of the invention. Since such guide rails are known in the art, they are not described in further detail for the sake of brevity.

In the illustrated embodiment, the lift sub-system 300 is a parallelogram lift system. In the illustrated embodiment, the lift sub-system 300 includes a first parallelogram 310 and a second parallelogram 320, parallel to one another. The first parallelogram 310 includes first horizontal link member 330a, a second horizontal link member 340a, a first vertical link member 350a, and a second vertical link member 360a. The first and second vertical link members 350a, 360a are pivotably connected to the first horizontal link member 330a at their first ends and to the second horizontal link member 340a at their second ends. Three of the four pivot joints 372a, 374a, and 376a are visible in FIG. 1. In an exemplary embodiment, the link members 330a, 340a, 350a, 360a may be made from composite materials such as G10 or FR4, by way of non-limiting examples only. Likewise, in an exemplary embodiment, the pivot joints may include plastic rods made of thermoplastic polyethylene such as Ultra-high-molecular-weight polyethylene (UHMW), by way of non-limiting example only. The second parallelogram 320 includes similar horizontal and vertical link members and pivot joints, which are not labeled for the sake of clarity. The first parallelogram 310 and the second parallelogram 320 are rigidly connected to one another such that they move in unison. In another embodiment, the lift sub-system may include more than or less than two parallelogram.

In the illustrated embodiment, the first horizontal link member 330a of the first parallelogram 310 is movably coupled to the guide rail 210. The first horizontal link member 330a may be controlled to move along the guide rail 210. In one embodiment, the first horizontal link member 330a includes a first plurality of rollers 382a and a second plurality of rollers 384a. The first horizontal link member 330a is mounted to the first guide rail 210 such that the first plurality of rollers 382a engage a first surface of the first guide rail 210 and the second plurality of rollers 384a engage a second surface of the first guide rail 210 opposite the first surface. Likewise, the first horizontal link member of the second parallelogram 320 is movably coupled to the second guide rail 220. In an exemplary embodiment, the rollers are made of non-metallic and non-conductive material such as a polymer, for example, urethane.

The patient bed system 100 further includes a platform motor drive 390 operatively connected to the first vertical link members of the first and second parallelograms 310, 320. In an exemplary embodiment, the platform motor drive 390 may include an electric drive, a hydraulic drive or a pneumatic drive with or without a gearbox. More particularly, the platform motor drive 390 is operatively connected to the first and second parallelogram systems 310, 320, for example via a motor shaft or a connecting shaft. The platform motor drive 390 may include any of a hydraulic, pneumatic, or an electric motor and can be a direct belt drive or a chain drive with or without a gear reduction system. When activated, the platform motor drive 390 causes the first vertical link members to pivot or incline relative to the corresponding first horizontal link members of the first and second parallelograms 310, 320.

While not shown in the drawing, a drive may be used to cause the first horizontal link member 330a to move along the first guide rail 210 along the longitudinal axis 230 with the first and second plurality of rollers 382a, 384a guiding and supporting the first horizontal link member 330a along the first guide rail 210. Such a drive can be an electric motor, or a hydraulic drive, or a pneumatic drive, by way of non-limiting examples.

The lift sub-system 300 is thus movably coupled to the guide sub-system 200, such that the lift sub-system and the associated bed sub-system 500 can move along the first longitudinal axis 230. The lift sub-system 300 is further configured to adjust the height of the bed sub-system 500 relative to the guide sub-system, as will be explained in detail below.

Still referring to FIG. 1, the carriage sub-system 400 includes a rotation block 410 (FIG. 2), a carriage 420, first and second guides 430, 440, a first connecting shaft 450 extending between first ends of the first and second guides and a second connecting shaft 460 extending between second ends of the first and second guides. In the illustrated embodiment, the rotation block 410 is pivotably mounted between the first and second parallelograms 310, 320. More particularly, in the illustrated embodiment, the rotation block 410 is aligned with the pivot joint 374a of the first parallelogram 310 and the corresponding pivot joint (not visible) of the second parallelogram 320. In a first operating state, the rotation block 410 may be secured such that there is no relative movement between the rotation block 410 and the second vertical link member 360a as well as the corresponding vertical link member of the second parallelogram 320. In a second operating state, the rotation block 410 may be permitted to pivot relative to the second vertical link member 360a and the corresponding vertical link member of the second parallelogram 320.

The carriage 420 is rigidly secured to the rotation block 410 such that there is no or little relative movement therebetween. In one configuration, the carriage 420 and the rotation block 410 may be in the form of a unitary structure. In an exemplary embodiment, the carriage 420 includes a first plurality of rollers 422a and a second plurality of rollers 424a along a first lateral side thereof and a third plurality of rollers and a fourth plurality of rollers along a second lateral side thereof. The first guide 430 is arranged between the first and second plurality of rollers 422a, 424a such that the first plurality of rollers 422a are in contact engagement with a first side of the first guide 430 and the second plurality of rollers 424a are in contact engagement with a second side of the first guide 430, opposite the first side. Similarly, the second guide 440 is arranged between the third and fourth plurality of rollers (not shown) such that the third plurality of rollers are in contact engagement with a first side of the second guide 440 and the fourth plurality of rollers are in contact engagement with the second side of the second guide 440, opposite the first side. In an exemplary embodiment, the rollers are made of non-metallic and non-conductive material such as a polymer, for example, urethane.

The first and second connecting shafts 450, 460 are rotatably mounted between the first and second guides 430, 440. The first connecting shaft 450 includes a first wheel 452 proximal to a first end thereof and a second wheel 454 proximal to a second end thereof. Likewise, the second connecting shaft 460 includes a first wheel 462 proximal to a first end thereof and a second wheel 464 proximal to a second end thereof. In an exemplary embodiment, the first and second connecting shafts 450, 460 may be mounted to the first and second guides 430, 440 using ball bearings, bush bearings, or equivalents so as to permit rotational movement of the first and second connection shafts relative to the first and second guides 430, 440.

Figure 6:
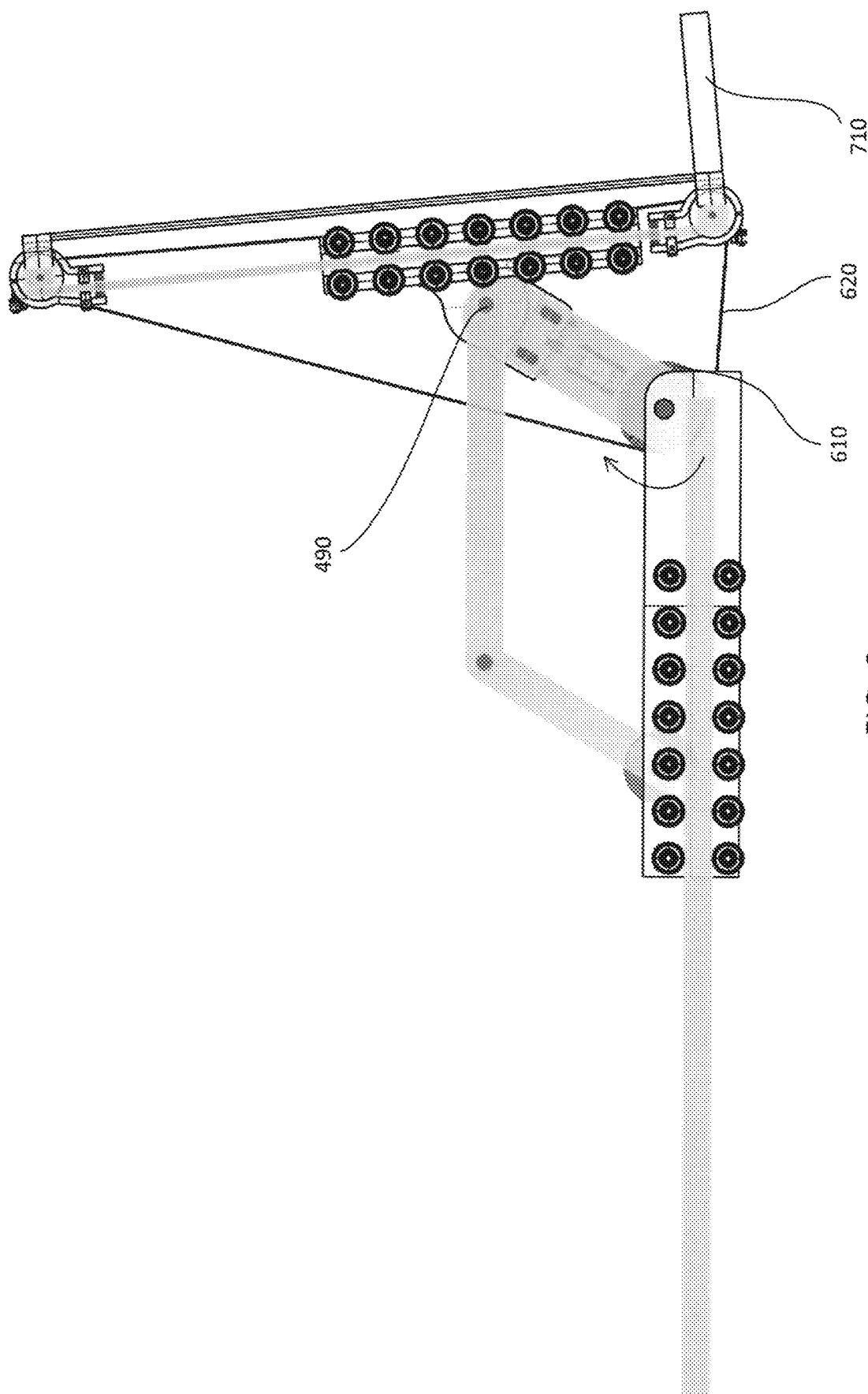
FIG. 6 shows a side view of patient positioning system with a foot plate according to an embodiment of the technology.

The carriage sub-system 400 also includes a support 470 (FIG. 4A), which is not illustrated in FIG. 1. The carriage sub-system 400 is mounted to the lift system 300 such that the carriage sub-system can move along a second longitudinal axis 480 and can rotate about a rotational axis 490, as will be explained in further detail below. In one configuration, the first longitudinal axis 230 and the second longitudinal axis 480 are parallel to one another, for example, as illustrated in FIG. 1. In other configurations, the first longitudinal axis 230 and the second longitudinal axis 480 may not be parallel to one another, for example, as illustrated in FIG. 6.

The patient positioning system 100 further includes a second motor drive system 600. In an exemplary embodiment, the second motor drive system 600 includes a motor drive 610 and a belt 620. While the example includes a belt 620, it will be understood that any actuator such a chain (preferably non-magnetic), a rope, and a cable, can be used instead, without departing from the scope of the disclosure.

In an exemplary embodiment, the motor drive 610 may include an electric drive, a hydraulic drive or a pneumatic drive with or without a gearbox. In an exemplary embodiment, the belt 620 may be made from an aramid fiber urethane composite, by way of non-limiting example only. At a first end, the belt 620 is rigidly secured to a first end of the carriage 420 and, at a second end, the belt 620 is rigidly secured to a second end of the carriage 420. The belt 620 engages the first connecting shaft 450 between the motor drive 610 and the first end of the carriage 420 and the second connecting shaft 460 between the motor drive 610 and the second end of the carriage 420. The second motor drive system 600 includes a rotation brake system 630 and a slab brake system 640.

Figure 2:
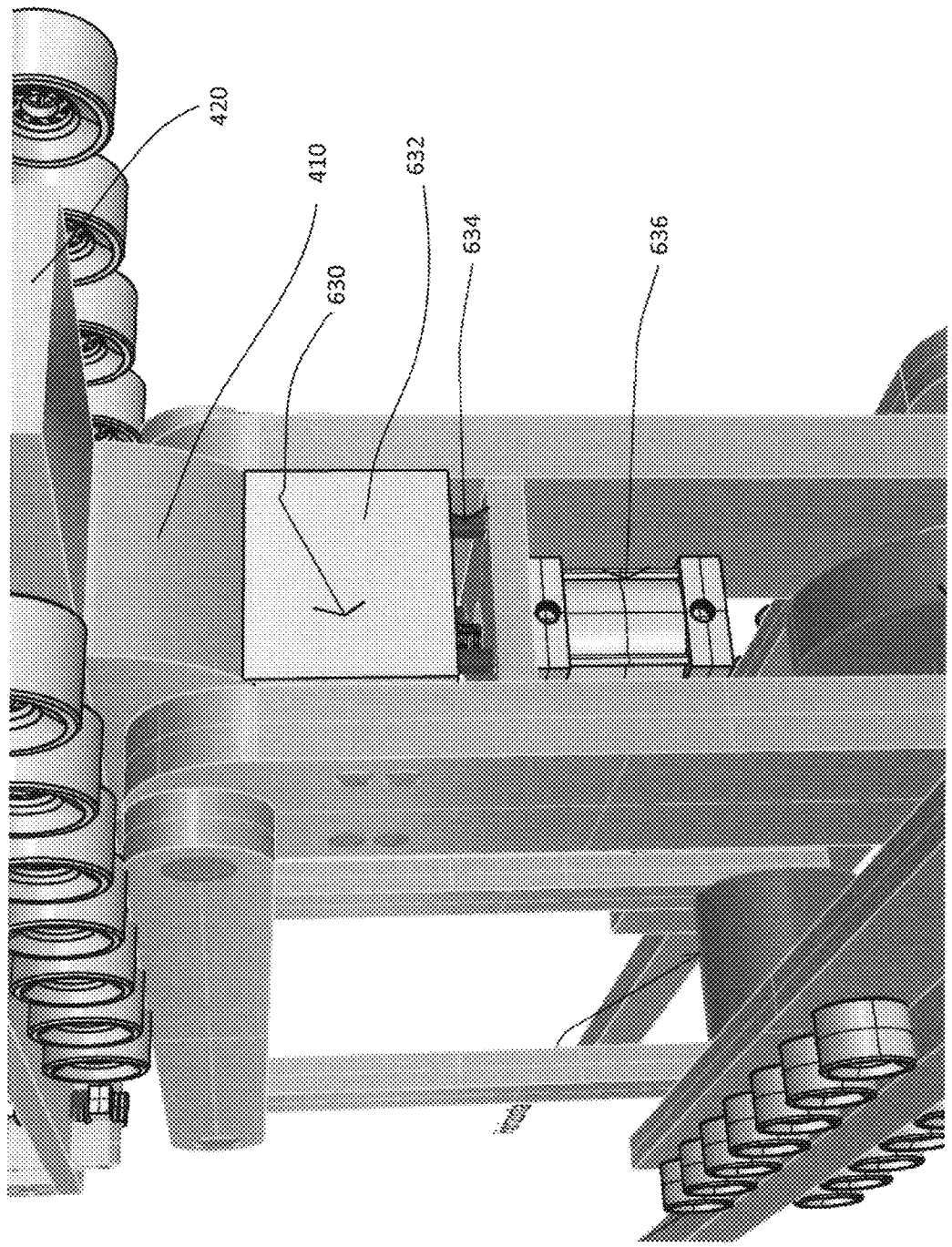
FIG. 2 shows a partial front isometric view of the patient positioning system of FIG. 1 illustrating a rotation brake system according to an embodiment of the technology.

Referring now to FIG. 2, the rotation brake system 630 includes a rotation brake block 632, brake block springs 634 and air cylinder 636. The rotation brake block 632 is arranged so as to selectively engage the rotation block 410. In an engaged state, the rotation brake block 632 inhibits a rotational movement of the rotation block 410. In a disengaged state, on the other hand, the rotation brake block 632 would permit a rotational movement of the rotation block 410. The rotation brake block 632 may be selectively engaged or disengaged with the aid of the brake block springs 634. In an exemplary embodiment, the brake block springs 634 are non-metallic and non-conductive springs, for example, rubber springs. The brake block springs 632, in turn, may be selectively activated or deactivated with the aid of the air cylinder 636. Such springs and air cylinders are known in the art and therefore are not described in further detail. It will be understood that the rotation brake system is not limited to the described block brake and springs. Other known brake mechanisms such as disc brakes, drum brakes, or locking pins may also be included in other embodiments for selectively engaging with or disengaging from the rotation block 410.

Figure 3:
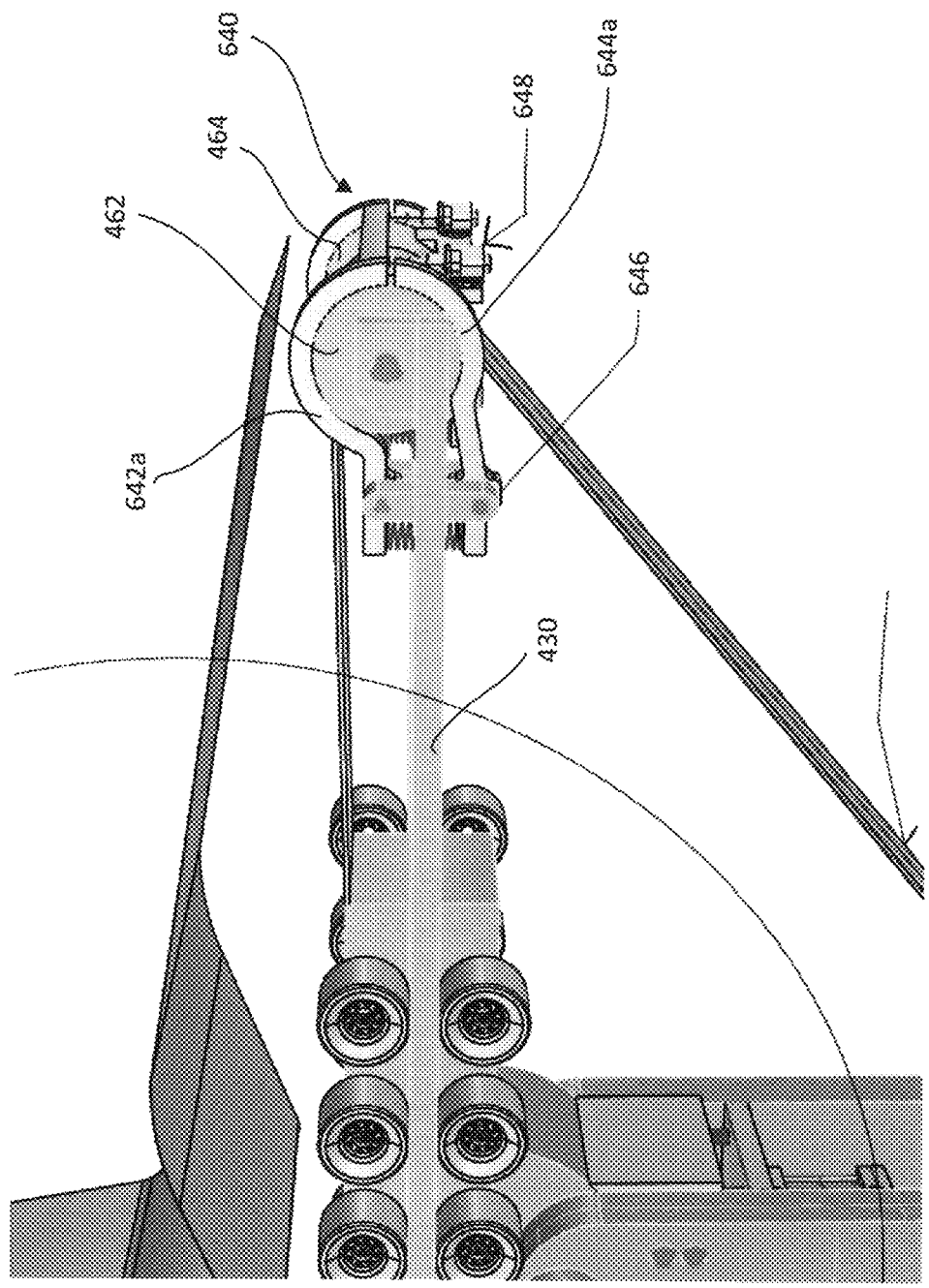
FIG. 3 shows a partial side view of the patient positioning system of FIG. 1 illustrating a slab bed brake system according to an embodiment of the technology.

Now referring to FIG. 3, the slab brake system 640 includes a first clamp brake element 642a and a second clamp brake element 644a. The first clamp brake element 642a and the second clamp brake element 644a envelope the first and second wheels 462 and 464 of the second connecting shaft 460 so as to selectively engage the first and second wheels 462, 464. In an engaged state, the first clamp brake element 642a and the second clamp brake element 644a collectively inhibit a rotational movement of the first and second wheels 462, 464. Since the first and second wheels 462, 464 are part of the second connecting shaft 460, a rotational movement of the second connecting shaft 460 would also be inhibited when the first clamp brake element 642a and the second clamp brake element 644a are in the engaged state. In a disengaged state, on the other hand, the first clamp brake element 642a and the second clamp brake element 644a would permit a rotational movement of the first and second wheels 462, 464. Since the first and second wheels 462, 464 are part of the second connecting shaft 460, a rotational movement of the second connecting shaft 460 would also be permitted when the first clamp brake element 642a and the second clamp brake element 644a are in the disengaged state. The first clamp brake element 642a and the second clamp brake element 644a may be selectively engaged or disengaged with the aid of the springs 646. In an exemplary embodiment, the springs 646 are non-metallic and non-conductive springs, for example, plastic springs. The springs 646, in turn, may be selectively activated or deactivated with the aid of the air pistons 648. While not labeled, the slab brake system 640 includes a third clamp brake element and a fourth clamp brake element enveloping the first and second wheels 452, 454 of the first connecting shaft 450, springs for selectively activating or deactivating the third and fourth clamp brake elements and air pistons for selectively activating or deactivating the springs.

Such springs and air pistons are known in the art and therefore are not described in further detail. It will be understood that the slab brake system is not limited to the described clamp brakes and springs. Other known brake mechanisms such as disc brakes, drum brakes, or locking pins may also be included in other embodiments for selectively inhibiting or permitting the rotational movement of the first and second wheels 462, 464 and the second connecting shaft 460 as well as the first and second wheels 452, 454 and the first connecting shaft 450.

Figure 4A:
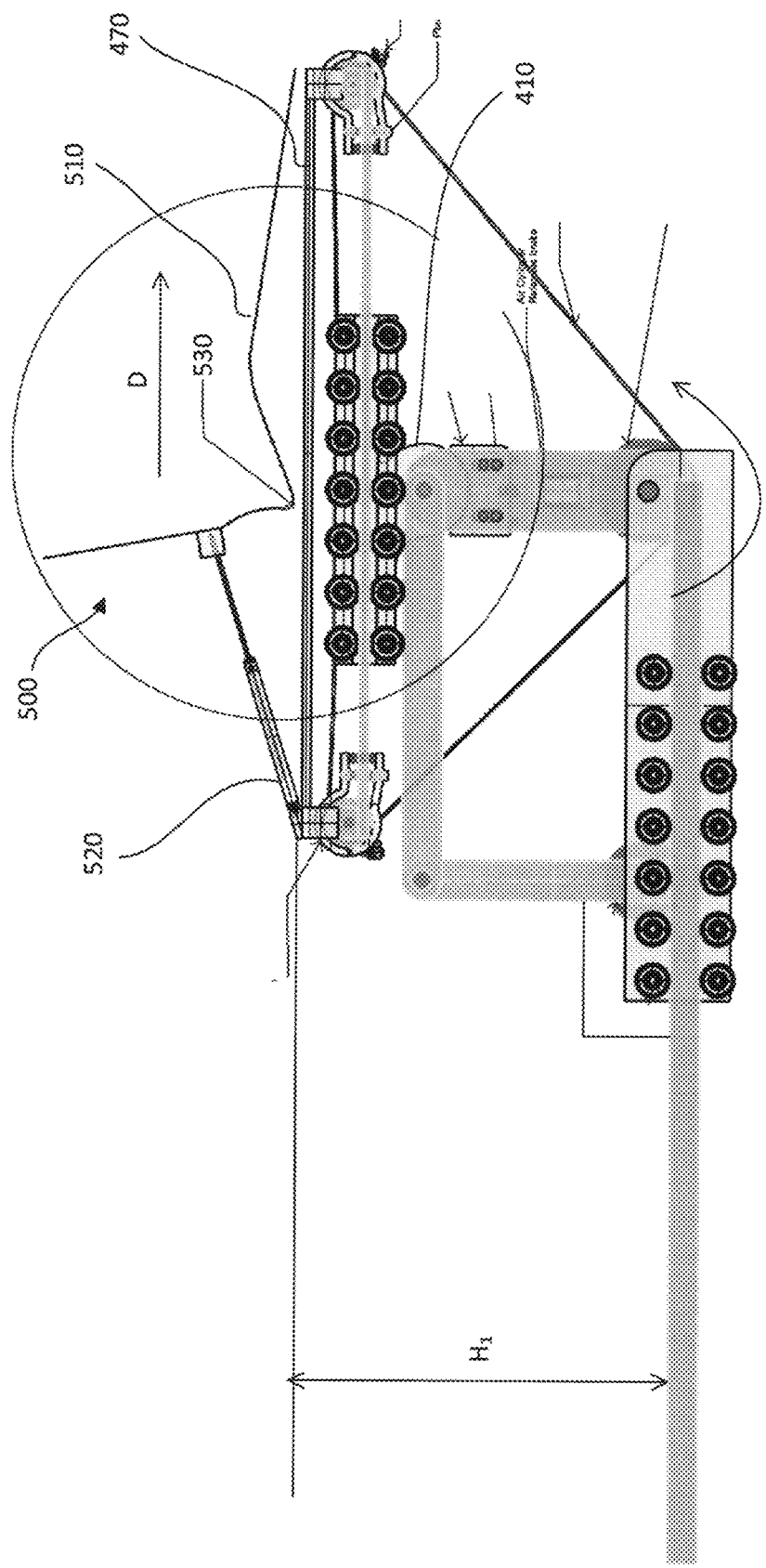
FIG. 4A shows a side view of a patient positioning system according to an embodiment of the technology.
Figure 4B:
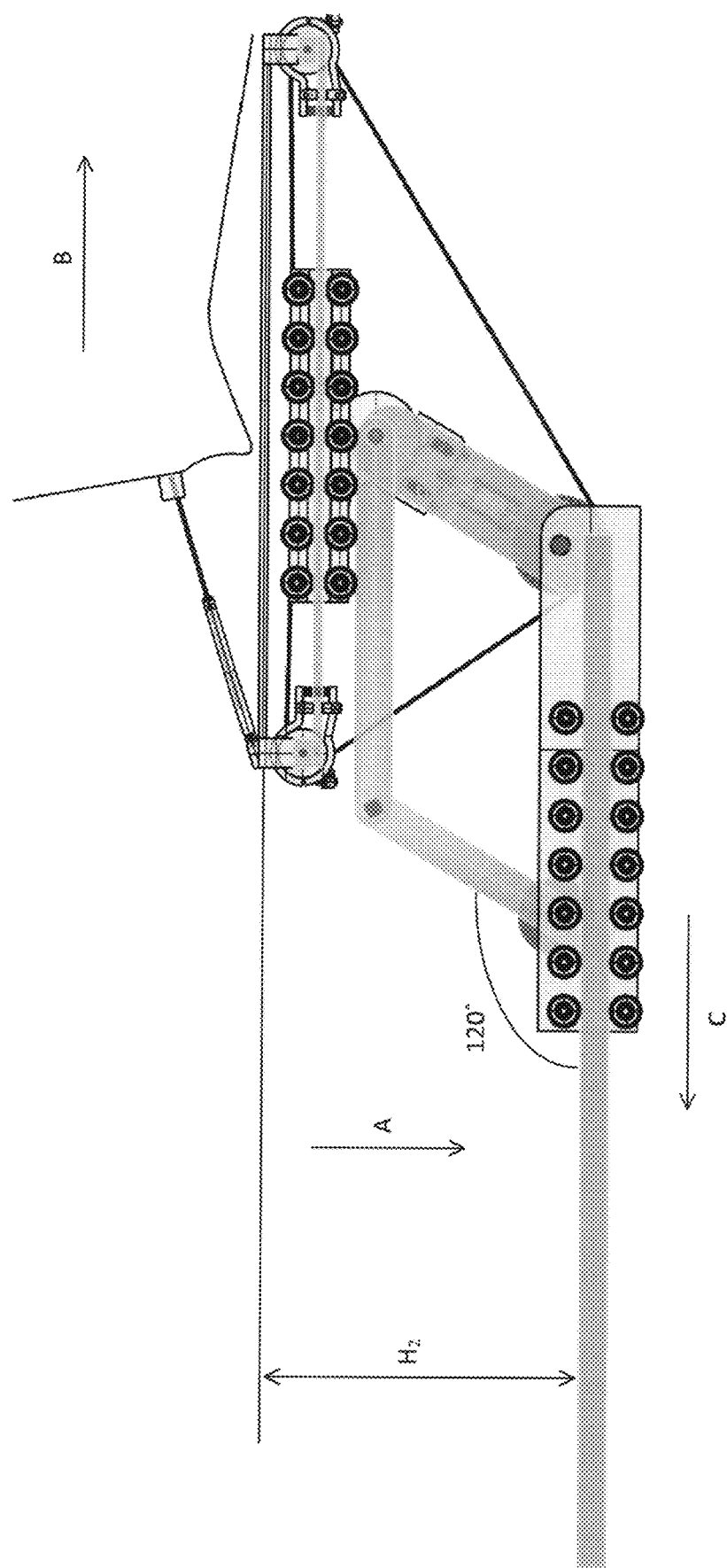
FIG. 4B shows a side view of the patient positioning system of FIG. 4A in a first lowered position according to an embodiment of the technology.
Figure 4C:
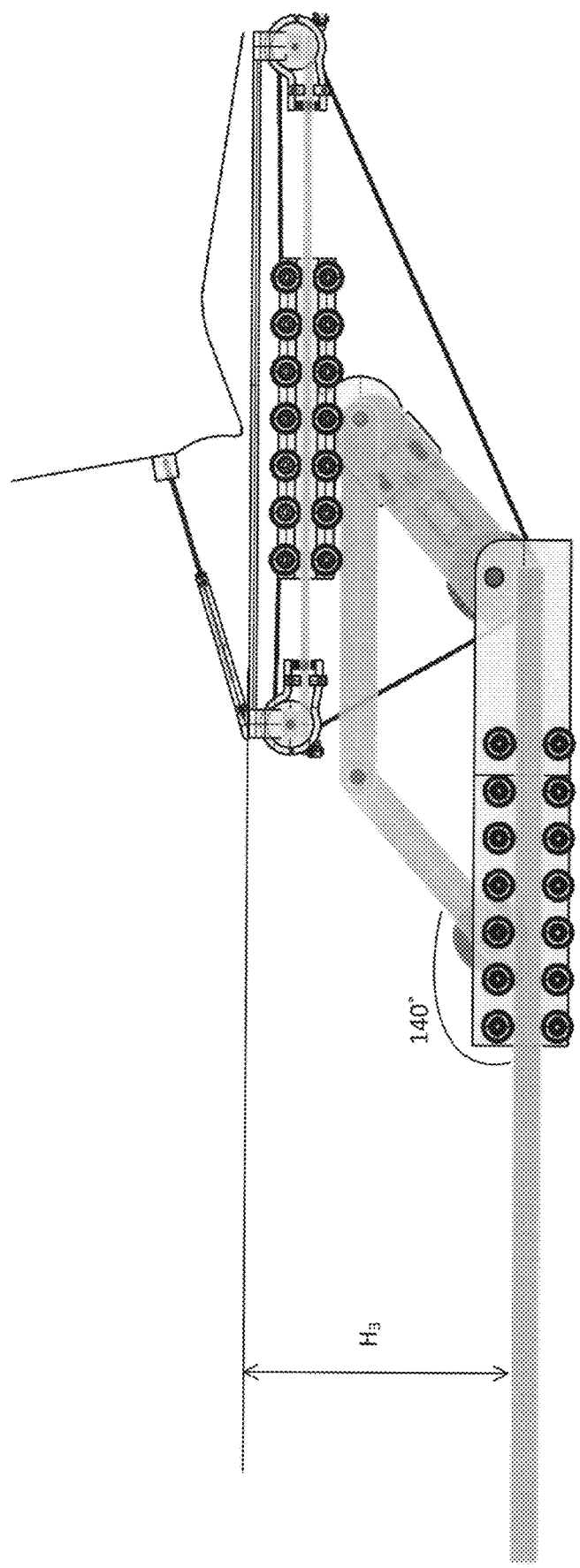
FIG. 4C shows a side view of the patient positioning system of FIG. 4A in a second lowered position according to an embodiment of the technology.
Figure 5:
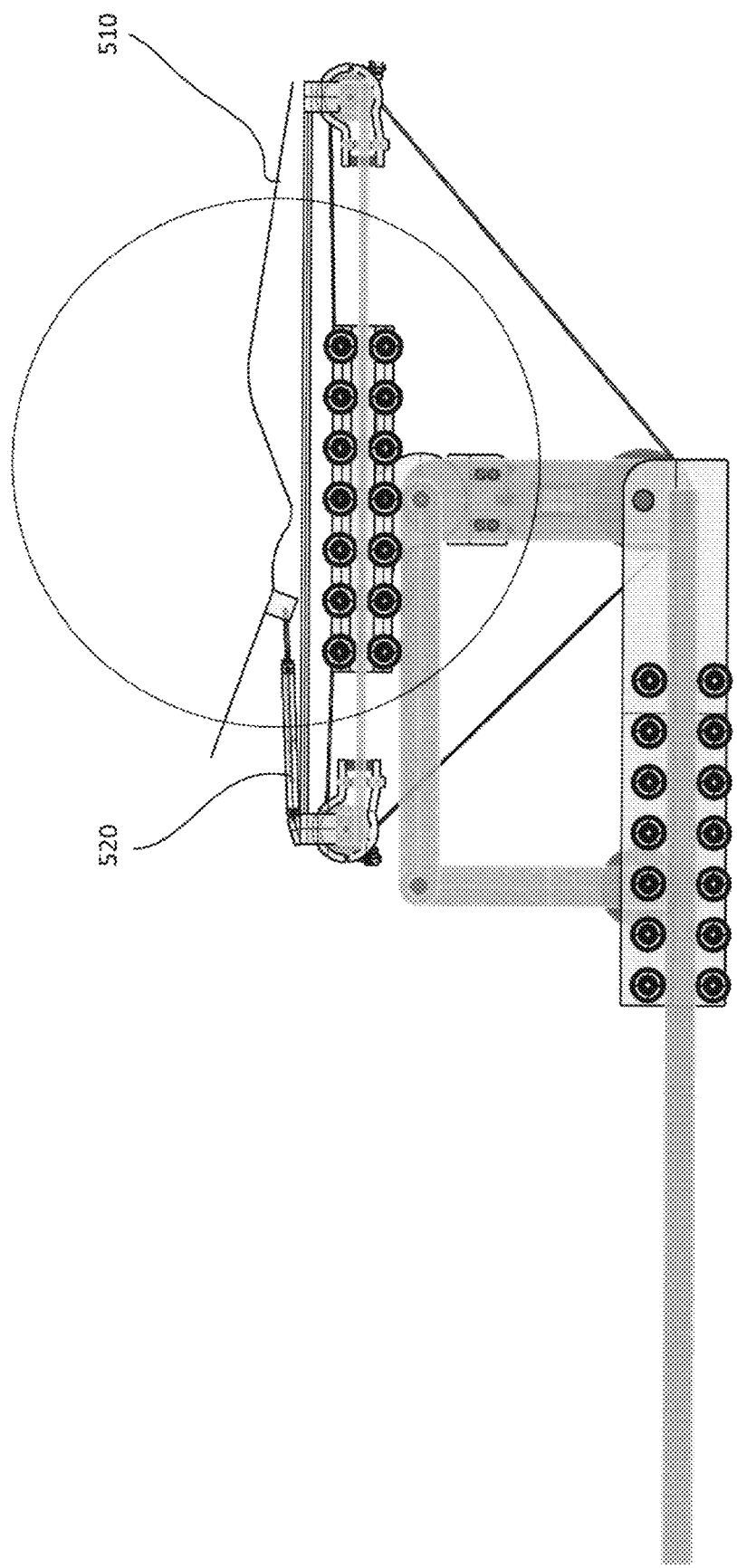
FIG. 5 shows a side view of the patient positioning system of FIG. 4A with a bed in a reclined position according to an embodiment of the technology.

Referring now to FIGS. 4A and 5, the bed sub-system 500 includes a reclinable bed 510 and reclining mechanism 520. In an exemplary embodiment, the reclinable bed 510 includes a hinge 530. The reclinable bed 510 may assume an upright chair configuration as illustrated in FIGS. 4A-4C in one operating state. In another state, the reclinable bed 510 may assume a substantially reclined bed configuration as illustrated in FIG. 5. It will of course be understood that the reclinable bed 510 may also assume any intermediate position between the upright chair configuration and the substantially reclined bed configuration. In yet other embodiment, the reclinable bed 510 may also assume a completely flat-bed configuration. In exemplary embodiment, the reclinable bed 510 may be made from a combination of materials such as polyvinyl chloride (PVC) and nylon. In one embodiment, the reclining mechanism 520 may take the form of a hydraulic system. The bed sub-system 500 is rigidly coupled to the support 470 of the carriage sub-system 400, such that there is no relative movement between the bed sub-system and the carriage sub-system. As such reclining beds and reclining mechanisms are known in the art, they are not described in further detail.

Referring now to FIGS. 4A-4C, the operation of the lift sub-system 400 will be described. The platform motor drive 390 is configured to drive the lift sub-system 400. In an exemplary embodiment, a motor shaft of the motor drive 390, or a connecting shaft operatively connected to the motor drive 390, is coupled to the first vertical link member 350*a* and the corresponding first vertical link member of the second parallelogram system 320 so as to pivot or incline them relative to the first horizontal link member 330*a* and the first horizontal link member of the second parallelogram, respectively, as well as relative to the first and second guide rails 210, 220. FIG. 4A illustrates the lift sub-system 400 in an inactivated state, wherein all the vertical link members are vertical and consequently the support 470 has a height $H_1$ relative to the first and second guide rails 210, 220. FIG. 4B illustrates the lift sub-system 400 in one activated state, wherein all the vertical link members are inclined at an angle of 120° and consequently the support 470 has a height $H_2$ relative to the first and second guide rails 210, 220. As will be understood, the height $H_2$ is smaller than the height $H_1$. FIG. 4C illustrates the lift sub-system 400 in another activated state, wherein all the vertical link members are inclined at an angle of 140° and consequently the support 470 has a height $H_3$ relative to the first and second guide rails 210, 220. As will be understood, the height $H_3$ is smaller than the height $H_2$ as well as $H_1$. It will further be appreciated that the vertical link members may be inclined at many other different angles to obtain a desired height of the support 470 and the bed sub-system 500 mounted on the support 470. An advantage of the parallelogram lift sub-system is that the height of the patient bed may be adjusted independent of the other sub-systems of the patient bed system 100. Another advantage of the parallelogram lift sub-system is that any metal and drive components such as pistons and electric motors in the lift platforms, which may either adversely affect the MRI system or may be adversely affected by the strong magnetic field of the MRI system, may be arranged outside the imaging space of an MRI scanner in the parallelogram systems.

FIG. 4B also illustrates that as all the vertical link members are inclined, the support 470 is lowered as depicted by an arrow A. Simultaneously, the support 470 is displaced away from the guide rails 210, 220 as shown by an arrow B. If it is desired that the support 470 maintain the same position relative to the guide rails 210, 220 while the height is lowered, all the horizontal link members may be moved, by the drive (not shown), along the first and second guide rails 210, 220 as shown by an arrow C to maintain or achieve a desired position of the support 470.

Referring now to FIGS. 1-3 and 6, the operation of the second motor drive system 600 will be described. The second motor drive system 600 may be used to rotate or pivot the bed sub-system 500 as well as to move the bed sub-system 500 along the longitudinal axis 480. This may be accomplished by selectively using either the rotation brake system 630 or the slab brake system 640. If it is desired to rotate the patient bed 510 about the rotational axis 490, the rotation brake system 630 is disengaged using the air cylinder 636, and the slab brake system 640 is engaged. More particularly, the rotation brake block 630 is disengaged from the rotation block 410 and all the first and second clamp brake elements are engaged with the corresponding wheels 462, 464, 452, 454 of the first and second connecting shafts 460, 450, respectively. Thus, when the motor drive 610 is activated in a clockwise direction, the belt 620 pulls the second connecting shaft 560 down and permits the first connecting shaft 540 to move up, thereby rotating the carriage sub-system 500 about the rotational axis 490 in a clockwise direction. It will be understood that if the motor drive 610 is activated in a counter clockwise direction, the belt 620 would pull the first connecting shaft 540 down and permit the second connecting shaft 560 to move up, thereby rotating the carriage sub-system 500 about the rotational axis 490 in a counter clockwise direction.

Referring now to FIG. 4A, the rotation brake system 630 is engaged and the slab brake system 640 is disengaged. More particularly, the rotation brake block 632 engages the rotation block 410 with the aid of the springs 634 and all the first and second clamp brake elements are disengaged from the corresponding wheels 462, 464, 452, 454 of the first and second connecting shafts 460, 450, respectively. Thus, the rotation of the rotation block 410 is inhibited. If the motor drive 610 is activated in a counter clockwise direction, the first and second guides 430, 440 slide along the first, second, third, and fourth plurality of rollers, respectively, and move the patient bed 510 forward as illustrated by an arrow D. If, on the other hand, the motor drive 610 is activated in a clockwise direction, the patient bed 510 is moved backwards. Thus, a single motor drive system 600 may be used to both rotate the patient bed 510 as well as move the patient bed along a longitudinal direction.

For sake of simplicity, FIG. 6 illustrates a foot plate 710 without the bed sub-system 500. It will, however, be understood that an embodiment of the invention may include both the bed sub-system 500 as well as the foot plate 710. It is further possible to adjust the height of the carriage sub-system 400 while maintaining a generally vertical orientation as illustrated in FIG. 6. To adjust the height of the carriage sub-system 400, the rotation brake system 630 is now engaged and the slab brake system 640 is disengaged. More particularly, the rotation brake block 632 engages the rotation block 410 with the aid of the springs 634 and all of the first and second clamp brake elements are disengaged with the wheels 462, 464, 452, 454 of the first and second connecting shafts 460, 450, respectively. Depending on the direction of activation of the motor drive 610, the foot plate 710 may be lowered or raised along the longitudinal axis 480.

Figure 7:
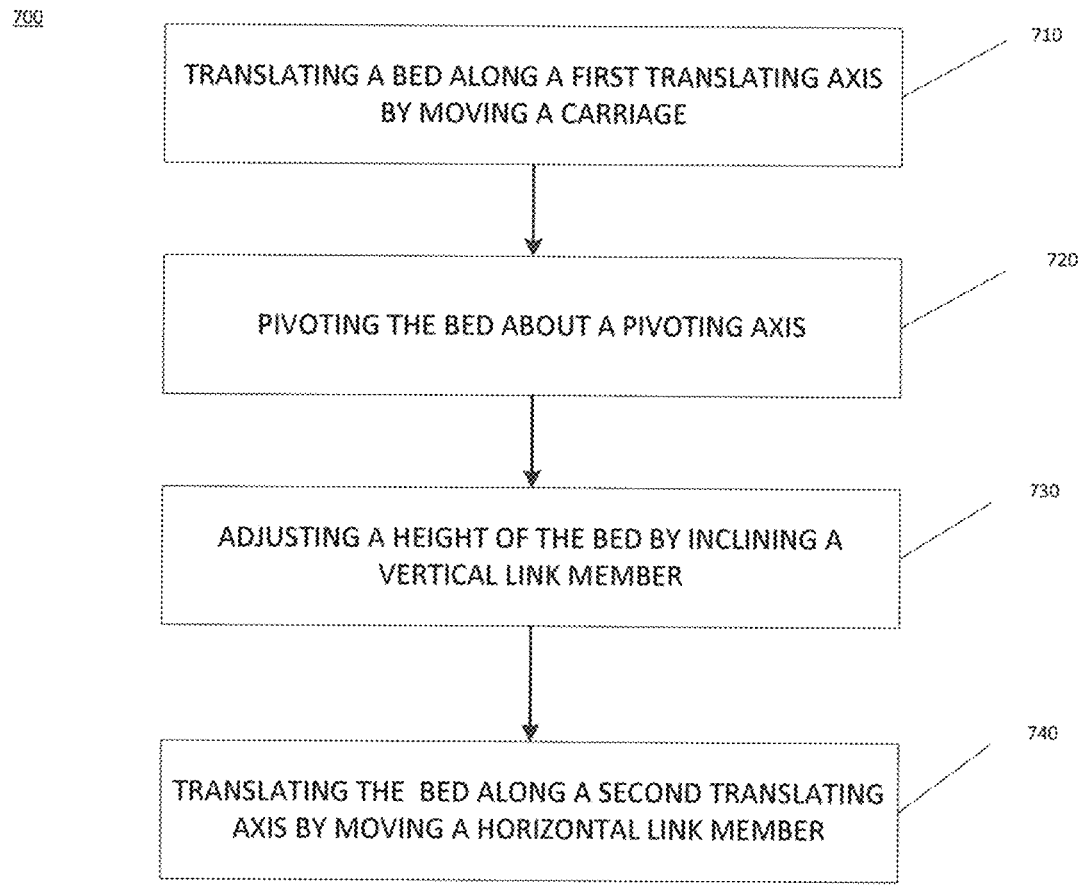
FIG. 7 shows a flow-chart of a method for positioning a patient bed according to an aspect of the technology.

Referring now to FIG. 7, a flow-chart of a method 700 of positioning a patient bed will be described. While the illustrated flow-chart includes several sequential steps, it will be understood that the steps can be performed in any order. Furthermore, one or more of these steps may also be performed simultaneously and one or more steps may be omitted as well. At block 710, the method includes translating the bed 510 along the first translational axis 480 by moving the carriage 420. (FIG. 4A) At block 720, the method includes pivoting the bed 510 about the pivoting axis 490. (FIG. 6) At block 730, the method includes adjusting a height of the bed 420 by inclining the first vertical link member 350a. (FIGS. 4B, 4C) Finally, at block 740, the method includes translating the bed 420 along a second translating axis 230 by moving the horizontal link member 330a along the first guide rail 210.

In one example, a patient positioning system includes:
at least one vertical link member;
a carriage sub-system rotatably mounted to the at least one vertical link member, the carriage sub-system comprising: a carriage having a first end and a second end; a first guide movably coupled to the carriage and having a first end and a second end; a second guide movably coupled to the carriage and having a first end and a second end; a first connecting shaft rotatably coupled to the first ends of the first guide and the second guide; a second connecting shaft rotatably coupled to the second ends of the first guide and the second guide;
a patient bed mounted to the carriage sub-system; and
a motor drive system comprising: a motor drive; a belt configured to be driven by the motor drive, the belt coupled at a first end to the first end of the carriage and at a second end to the second end of the carriage, the belt being in contact engagement with the first connecting shaft between the motor drive and the first end of the carriage and with the second connecting shaft between the motor drive and the second end of the carriage; a rotation brake system configured to selectively engage with or disengage from the carriage; and a slab brake system configured to selectively engage with or disengage from the first and second connecting shafts; and/or
a lift sub-system configured to adjust a height of the carriage sub-system, the lift sub-system comprising: a parallelogram comprising: the at least one vertical link member; a second vertical link member; a first horizontal link member; and a second horizontal link member, wherein the at least one vertical link member and the second vertical link member are pivotably connected to the first and second horizontal link members.

The technology embodied in the patient positioning system described above may find use in MRI systems. It may be used during imaging to provide improvements in positioning patients in a variety of positions suited for measurement of the particular anatomy of interest. The added flexibility allows for positioning patients in positions that may allow for revealing and/or accurate imaging of the anatomy of interest as the patient may be more stably positioned and supported in a position that is required for imaging, e.g., knees angled in a non-weight bearing position in the case of a sports injury so that the internal areas of the knee may be the focus of the imaging. In addition to MRI systems, the positioning system may also find use in other clinical applications Although the technology herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A patient positioning system comprising:
at least one vertical link member having a first end and a second end;
at least one horizontal link member coupled to the at least one vertical link member and having a first end;
a carriage sub-system mounted to the at least one vertical link member, the carriage sub-system comprising:
a carriage having a first end and a second end;
a patient bed sub-system mounted to the carriage; and
a drive system comprising:
an actuator configured to selectively drive the carriage to rotate or pivot the patient bed sub-system about a rotational axis to move the patient bed sub-system along a longitudinal axis, wherein the actuator is coupled at a first end to the first end of the carriage and at a second end to the second end of the carriage, the first rotational axis extending across the first end of the at least one vertical link member and the first end of the at least one horizontal link member;
a drive configured to drive the actuator and associated with the second end of the at least one vertical link member; and
a slab brake system configured to selectively constrain a motion of the actuator,
wherein the carriage is pivotably mounted to the at least one vertical link member, and
wherein the system further comprises a rotation brake system configured to selectively engage with the carriage,
wherein the carriage sub-system further comprises a rotation block pivotably mounted between the first and second parallelograms,
wherein in a first operating state, the rotation block is secured such that there is no relative movement the rotation block and the second and fourth vertical link members, and
wherein in a second operating state, the rotation block is configured to pivot relative to the second and fourth vertical link members, and
wherein the rotation brake system comprises:
a rotation brake block configured to selectively engage the rotation block;
a brake block spring configured to select urge the rotation brake block against the rotation block; and an air cylinder configured to selectively actuate the brake block spring.

2. The system according to claim 1,
wherein the carriage sub-system comprises:
a first guide movably coupled to the carriage and having a first end and a second end;

a second guide movably coupled to the carriage and having a first end and a second end;

a first connecting shaft rotatably coupled to the first ends of the first guide and the second guide;

a second connecting shaft rotatably coupled to the second ends of the first guide and the second guide.

3. The system according to claim 2, wherein the actuator is in contact engagement with the first connecting shaft between the motor drive and the first end of the carriage and with the second connecting shaft between the motor drive and the second end of the carriage, and wherein the slab brake system is configured to selectively engage with the first and second connecting shafts to constrain the motion of the actuator.

4. The system according to claim 2, wherein the carriage comprises:

a first plurality of rollers and a second plurality of rollers along a first lateral side of the carriage; and a third plurality of rollers and a fourth plurality of rollers along a second lateral side of the carriage, wherein the first guide is arranged between the first plurality of rollers and the second plurality of rollers, and wherein the second guide is arranged between the third plurality of rollers and the fourth plurality of rollers.

5. The system according to claim 4, wherein the first connecting shaft comprises a first wheel proximal to a first end thereof and a second wheel proximal to a second end thereof, and wherein the second connecting shaft comprises a third wheel proximal to a first end thereof and a fourth wheel proximal to a second end thereof.

6. The system according to claim 5, further comprising:

a first clamp brake element enveloping the first wheel;

a second clamp brake element enveloping the second wheel;

a third clamp brake element enveloping the third wheel; and a fourth clamp brake element enveloping the fourth wheel.

7. The system according to claim 6, further comprising:

a first spring configured to selectively activate the first clamp brake element;

a second spring configured to selectively activate the second clamp brake element;

a third spring configured to selectively activate the third clamp brake element; and a fourth spring configured to selectively activate the fourth clamp brake element.

8. The system according to claim 7, further comprising:

a first air piston configured to selectively actuating the first spring;

a second air piston configured to selectively actuating the second spring;

a third air piston configured to selectively actuating the third spring; and a fourth air piston configured to selectively actuating the fourth spring.

9. The system according to claim 1, further comprising:

a lift sub-system configured to adjust a height of the carriage sub-system, the lift sub-system comprising:

a first parallelogram comprising:

the at least one vertical link member;

a second vertical link member;

the at least one first horizontal link member; and a second horizontal link member parallel to the at least one first horizontal link member, wherein each of the at least one vertical link member and the second vertical link member is pivotably connected to the first horizontal link member and the second horizontal link member.

10. The system according to claim 9, wherein the lift sub-system further comprises:

a second parallelogram parallel to and rigidly connected to the first parallelogram, the second parallelogram comprising:

a third vertical link member parallel to the at least one vertical link member and pivotably connected to the carriage sub-system;

a fourth vertical link member parallel to the second vertical link member;

a third horizontal link member parallel to the first horizontal link member; and a fourth horizontal link member parallel to the second horizontal link member, wherein the third vertical link member and the fourth vertical link member are pivotably connected to the third horizontal link member and the fourth horizontal link member.

11. The system according to claim 10, further comprising:

a first guide rail; and a second guide rail, wherein the first horizontal link member is movably coupled to the first guide rail, and wherein the third horizontal link member is movably coupled to the second guide rail.

12. The system according to claim 10, further comprising:

a drive operatively connected to the first vertical link member and the third vertical link member.

13. The system according to claim 12, wherein the first horizontal link member comprises a first plurality of rollers and a second plurality of rollers, and wherein the first horizontal link member is mounted to the first guide rail such that the first plurality of rollers engage a first surface of the first guide rail and the second plurality of rollers engage a second surface of the first guide rail opposite the first surface.

14. The system according to claim 1, wherein the patient bed sub-system comprises:

a reclinable bed; and a reclining mechanism configured to control the reclinable bed.

15. The system according to claim 14, wherein the reclinable bed comprises a hinge such that the reclinable bed is configured to assume at least:

an upright chair configuration in a first operational state;

a substantially reclined bed configuration in a second operational state; and an intermediate position between the upright chair configuration and the substantially reclined bed configuration in a third operational state.

* * * * *